(12) United States Patent
Chapuis et al.

(10) Patent No.: US 8,841,488 B2
(45) Date of Patent: Sep. 23, 2014

(54) KETONES AS PERFUMING INGREDIENTS

(71) Applicant: Firmenich SA, Geneva (CH)

(72) Inventors: Christian Chapuis, Mies (CH);
Anthony Birkbeck, Chambesy (CH);
Maurus Marty, Seon (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/043,428

(22) Filed: Oct. 1, 2013

(65) Prior Publication Data

US 2014/0030204 A1    Jan. 30, 2014

Related U.S. Application Data

(62) Division of application No. 12/920,703, filed as application No. PCT/IB2009/051550 on Apr. 14, 2009.

(30) Foreign Application Priority Data

Apr. 17, 2008 (EP) .................................... 08007519

(51) Int. Cl.
| C07C 49/00 | (2006.01) |
| C07C 403/08 | (2006.01) |
| C11D 3/50 | (2006.01) |
| C11B 9/00 | (2006.01) |
| C07C 49/21 | (2006.01) |
| C07C 403/16 | (2006.01) |
| C07C 45/00 | (2006.01) |
| A61Q 15/00 | (2006.01) |
| A61K 8/37 | (2006.01) |

(52) U.S. Cl.
CPC .............. *A61Q 15/00* (2013.01); *C07C 403/08* (2013.01); *C11D 3/50* (2013.01); *C11B 9/0034* (2013.01); *C07C 49/21* (2013.01); *C11B 9/003* (2013.01); *C07C 403/16* (2013.01); *C07C 45/004* (2013.01); *C07C 2101/14* (2013.01); *C07C 2101/16* (2013.01); *A61K 8/375* (2013.01)
USPC ....................................................... 568/376

(58) Field of Classification Search
None
See application file for complete search history.

(56) References Cited

U.S. PATENT DOCUMENTS

| 4,036,774 A | 7/1977 | van Ouwerkerk et al. .... 510/102 |
| 5,248,831 A | 9/1993 | Hopp et al. .................... 568/376 |
| 6,184,419 B1 | 2/2001 | Berg-Schultz et al. ........ 568/374 |
| 6,251,463 B1 * | 6/2001 | Rossy et al. ................... 426/533 |
| 2004/0131648 A1 | 7/2004 | deLong et al. ................. 424/401 |
| 2008/0032913 A1 * | 2/2008 | Finke et al. ......................... 512/6 |

FOREIGN PATENT DOCUMENTS

| EP | 0 520 290 A2 | 12/1992 |
| NL | 6918228 A | 6/1971 |

OTHER PUBLICATIONS

International Search Report and Written Opinion, Appl. No. PCT/IB2009/051550, Jul. 6, 2009.
Chung et al., "Volatile Components in Commercial Imitation Crabmeats," Food Science and Biotechnology 11(4):421-426 (2002).
Erman et al., "Some Features of the Rearrangement of Tertiary Ethynylcarbinols in the Presence of Polyvanadioorganosiloxanes," J. Org. Chem. USSR (English translation), pp. 21-28 (Jan. 1980).
Margathe et al., "Solid-Phase, Multicomponent Reactions of Methyleneaziridines: Synthesis of 1,3-Disubstituted Propanones," Organic Letters 7(22):4987-4990 (2005).
Wang et al., "Palladium-Catalyzed Intramolecular Hydroalkylation of Unactivated Olefins with Dialkyl Ketones," Organic Letters 5(15):2699-2701 (2003).
Yoshioka et al., "Studies on Stable Free Radicals. VIII. The Synthesis and Oxidation of Hindered 4-Oxopiperidine Derivatives," Bulletin of the Chemical Society of Japan 45(2):636-638 (1972).

\* cited by examiner

*Primary Examiner* — Rosalynd Keys
*Assistant Examiner* — Jennifer C Sawyer
(74) *Attorney, Agent, or Firm* — Winston & Strawn LLP

(57) ABSTRACT

A method to confer, enhance, improve or modify the odor properties of a perfuming composition or of a perfumed article by adding to the composition or article an effective amount of at least one compound of formula I:

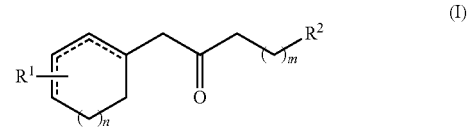

wherein n represents 0, 1 or 2; m represents 0, 1 or 2; the dotted lines represent only single bonds or one double bond and two single bonds; $R^1$ represents a hydrogen atom or a methyl or ethyl group, and $R^2$ represents an $OR^3$ group, $R^3$ representing a $C_1$-$C_3$ alkyl or alkenyl group; a group of formula $CR^4$=$C(R^4)_2$, or a group of formula

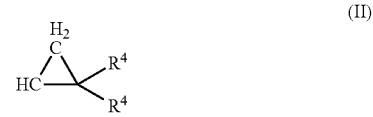

with $R^4$ representing a hydrogen atom or a methyl or ethyl group. These compounds impart a clean and natural fruity, pineapple odor type to the perfuming compositions or perfumed articles to which they are added.

14 Claims, No Drawings

KETONES AS PERFUMING INGREDIENTS

CROSS-REFERENCE TO RELATED APPLICATIONS

This application is a division of U.S. application Ser. No. 12/920,703 filed Sep. 2, 2010, which is the 371 filing of International application no. PCT/IB2009/051550 filed Apr. 14, 2009, which claims priority of European application 08007519.5 filed Apr. 17, 2008.

TECHNICAL FIELD

The present invention relates to the field of perfumery. More particularly, it concerns the use as perfuming ingredient of some ketone derivatives of formula (I), as shown herein below. The present invention concerns also the compositions or articles containing said compounds (I) as well as some of said compounds (I).

PRIOR ART

Some of the present compounds are known chemicals, for example: 1-cyclohexyl-5-hexen-2-one is reported by J. F. Margathe et al., in *Org. Lett.*, 2005, 7, 4987; 1-cyclopentyl-3-ethoxy-2-propanone is reported by H. Y. Chung et al., in *Food Science and Biotechnology*, 2002, 11, 421.

However, all the known compounds of the present invention have been reported as chemical intermediates or chemical products and, to the best of our knowledge, none of said compounds (I) has been reported in the prior art as having an odor or even an interest for the perfumery industry. Furthermore, the prior art documents do not report or suggest any organoleptic properties of the compounds of formula (I), or any use of said compound in the field of perfumery.

The compounds with the closest chemical structure and being described as having valuable organolepic properties are those reported in U.S. Pat. No. 6,184,419, and in particular 2-cyclohexyl-1,6-heptadien-3-one. However these prior art compounds are reported as having a green-galbanum or galbanum odor type, in other words a quite different note of the floral type. Nothing in the prior art suggests that the invention's compounds could have their specific odor (as reported further below) or even an odor at all.

SUMMARY OF THE INVENTION

The invention relates to a method

DESCRIPTION OF THE INVENTION

We have now surprisingly discovered that a compound of formula

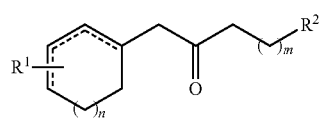

(I)

wherein n represents 0, 1 or 2;
m represents 0, 1 or 2;
one dotted line represents a single or double carbon-carbon bond and the two other dotted lines represent a single carbon-carbon bond;
$R^1$ represents a hydrogen atom or a methyl or ethyl group, said $R^1$ group being located at any of the position of the cyclic moiety;
$R^2$ represents a
  $OR^3$ group, $R^3$ representing a $C_1$-$C_3$ alkyl or alkenyl group;
  a group of formula $CR^4=C(R^4)_2$, $R^4$ representing, simultaneously or independently from each other, a hydrogen atom or a methyl or ethyl group; or
  a group of formula

(II)

$R^4$ having the same meaning as above;
can be used as perfuming ingredient, for instance to impart a clean and natural fruity, pineapple odor type.

In fact, the odor of the compounds of the present invention can vary according to the exact structure of the specific derivative, however all said compounds possess an amyl and/or pineapple odor type, and are devoid of galbanum notes, or do not evoke said galbanum notes, to the contrary of the compounds cited in U.S. Pat. No. 6,184,419.

According to a particular embodiment of the invention, said compounds (I) are those wherein n represents 0, 1 or 2; m represents 0, 1 or 2;
one dotted line represents a single or double carbon-carbon bond and the two other dotted lines represent a single carbon-carbon bond;
$R^1$ represents a hydrogen atom or a methyl group, said $R^1$ group being located at any of the position of the cyclic moiety;
$R^2$ represents a
  $OR^3$ group, $R^3$ representing a $C_1$-$C_3$ alkyl or alkenyl group;
  a group of formula $CR^4=C(R^4)_2$, $R^4$ representing, simultaneously or independently from each other, a hydrogen atom or a methyl group.

According to another particular embodiment of the invention, said compounds (I) are those

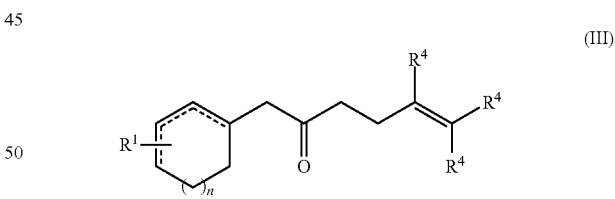

(III)

wherein n represents 0 or 1;
one dotted line represents a single or double carbon-carbon bond and the two other dotted lines represent a single carbon-carbon bond;
$R^1$ represents a hydrogen atom or a methyl group, said $R^1$ group being located at any of the position of the cyclic moiety;
$R^4$ representing, simultaneously or independently from each other, a hydrogen atom or a methyl group.

For the sake of clarity, by the expression "wherein one dotted line represents a single carbon-carbon bond and the two other a single or double carbon-carbon bond", or the similar, it is meant the normal meaning understood by a person skilled in the art, i.e. that the whole bonding (solid and dotted lines) between the carbon atoms connected by said dotted line, e.g. carbon 2 and 3, is a carbon-carbon single or double bond.

Some of the compounds (I) are also an object of the present invention since they are also novel compounds, and in particular those of formula

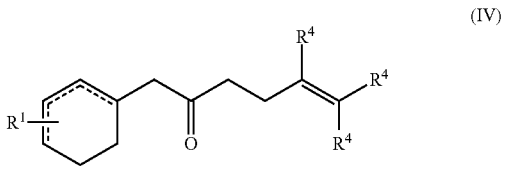

(IV)

wherein one dotted line represents a single or double carbon-carbon bond and the two other dotted lines represent a single carbon-carbon bond;
$R^1$ represents a hydrogen atom or a methyl group, said $R^1$ group being located at any of the position of the cyclic moiety;
$R^4$ representing, simultaneously or independently from each other, a hydrogen atom or a methyl group.

According to any one of the above embodiments of formula (I), (III) or (IV), at least two $R^4$ represent a hydrogen atom. According to any one of the above embodiments of formula (I), (III) or (IV), each $R^4$ represents a hydrogen atom. According to any one of the above embodiments of formula (I), (III) or (IV), $R^1$ represents a hydrogen atom. According to any one of the above embodiments of formula (I), (III) or (IV), each dotted line represents a single bond.

Amongst the invention's compounds, one may cite 1-cyclohexyl-5-hexen-2-one, which is one of the most appreciated by the perfumer. This compound possesses a very natural pineapple odor, with a very subtle and natural violet leaves tonality. Said compound is remarkable for combining with elegance and naturalness a very powerful and long-lasting performance in various application.

Other compounds of formula (I) are also described in Table (I) herein below, together with their odors:

TABLE 1

Structure and odor characteristics of the invention's compounds

| Structure of compound (I) | Odor |
|---|---|
| | Pineapple, allylic, much fruitier and less green than ether PHA, hop. |
| | Pineapple, allylic but less sweet, valerianic. |
| | Pineapple, fruity, honey, reminding somehow of allyl phenoxyacetate (Arctander N° 91). |

The organoleptic properties of compounds (I), and in particular 1-cyclohexyl-5-hexen-2-one, are closer to the olfactive family of the allylic derivative (known for their fruity-pineapple notes), but possess a proper distinct character.

Indeed the odor of compounds (I), e.g. the ones mentioned above and in particular 1-cyclohexyl-5-hexen-2-one, distinguishes itself from all the previously known analogues by lacking, or not having significant, galbanum notes (i.e., an aromatic bitter note), as well as any metallic note.

Furthermore, said compounds (I) are less sweet and more pineapple, and therefore more balanced and elegant, than the known allylic derivatives. Similarly, compounds (I) possess a green aspect much less developed and are fruitier than the glycolate derivatives.

In fact, compounds (I), and in particular 1-cyclohexyl-5-hexen-2-one, are an ideal compromise between the fruity notes of the allylic derivatives and the green aspect of the glycolate, i.e. the odors are not too sweet, as for the allyl compounds, and devoid of the metallic notes of the glycolates.

Finally, the odor of the invention's compounds distinguishes from the structural analogues disclosed in U.S. Pat. No. 6,184,419, by lacking the galbanum, metallic notes, which are so characteristic of the prior art compounds. In fact, the invention's compounds and the prior art analogues have simply a different odor, and said differences lend this two types of compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). In particular, said method is to impart odor notes as mentioned above for the invention's compounds, in particular to impart clean and natural fruity, pineapple odor type, and lacking galbanum notes.

By "use of a compound of formula (I)" it has to be understood here also the use of any composition containing compound (I) and which can be advantageously employed in perfumery industry as active ingredients.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOW-ANOL® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and ii) a consumer product base;

is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 15% by weight, or even more, of the compounds of the invention based on the weight of the composition into which they are incorporated. Concentrations lower than these, such as in the order of 0.001% to 3% by weight, can be used when these compounds are incorporated into perfumed articles, percentage being relative to the weight of the article.

The invention's compounds can be prepared according to the methods described herein below in the examples.

EXAMPLES

The invention will now be described in further detail by way of the following examples, wherein the abbreviations

Example 1

Synthesis of Compounds of Formula (I) by Using the Aldol Derivative of α-Damascone as Starting Material a) 1-Cyclohexyl-5-hexen-2-one

A solution of 1-cyclohexyl-5-hexen-2-ol (2.75 g, 15 mmol; prepared according to X. Wang et al, in *Org. Lett.*, 2003, 5, 2699, supplementary materials) in $CH_2Cl_2$ (5 ml) was added to a suspension of PCC (4.9 g, 22 mmol) and Celite® (7.35 g) in $CH_2Cl_2$ (70 ml) at 20°. After 4 hours at that temperature, 10 mol % of PCC was added and after a supplementary hour $Et_2O$ was added and the reaction filtrated over $SiO_2$ before to be concentrated. Purification by chromatography on silica with cyclohexane/AcOEt 95:5 afforded the desired ketone in 73% yield.

B.p. 69°/0.3 mbar.

IR: 3078, 2921, 2851, 1711, 1641, 1447, 1408, 1359, 1283, 1210, 1141, 1082, 996, 910.

$^1$H-NMR: 5.80 (tdd, J=7.0, 10.2, 17.1, 1H); 5.02 (dq, J=1.8, 17.1, 1H); 4.97 (dq, J=1.8, 10.2, 1H); 2.48 (t, J=7.4, 2H); 2.32 (t, J=7.0, 2H); 2.27 (d, J=7.0, 2H); 1.83 (m, 1H); 1.66, (m, 5H); 1.27 (m, 2H); 1.13 (m, 1H); 0.91 (m, 2H).

$^{13}$C-NMR: 210.1 (s); 137.2 (d); 115.1 (t); 50.6 (t); 42.5 (t); 33.9 (d); 33.3 (2t); 27.8 (t); 26.2 (t); 26.1 (2t).

b) 1-(1-Cyclohex-1-enyl)-5-hexen-2-one

Preparation of Butenyl Magnesium Bromide

The Grignard reagent was prepared by adding a solution of 4-bromo-1-butene (18.34 g, 135.9 mmol) in anhydrous THF (20 ml) to a suspension of magnesium metal shavings (4.00 g, 166.7 mmol) in anhydrous THF (100 ml) at ambient temperature. After the initiation of the exothermic reaction, the temperature was maintained between 28-32° C. by means of a water bath. Following the introduction of the bromo butene, the mixture was stirred for a further 60 minutes at ambient temperature. Additional THF (20 ml) was added to the reaction medium, and the Grignard solution titred 0.64 M. This solution was then used as a stock solution for the following experiments.

Preparation of 1-(1-cyclohex-1-enyl)-5-hexen-2-ol

The above-prepared butenyl Grignard reagent (0.64 m in THF, 15.12 ml, 9.67 mmol) was added slowly drop wise to a stirred solution of 1-(1-cyclohex-1-enyl)-acetaldehyde, (1.0 g, 5.6 mmol; prepared according to Erman, M. B, *J. Org. Chem. USSR* (EN Trans), 1980, 21-28) in THF (10 ml) cooled in a water bath. After 5 minutes, the reaction medium was poured into saturated ammonium chloride, and extracted twice with diethyl ether, washed with water then brine, dried over anhydrous sodium sulfate, filtered and the solvents removed in vacuo. The crude product was further purified by bulb to bulb distillation, 125° C. at 0.35 mbar, to give 0.75 g, 74% yield.

$^1$H NMR: 5.83 (ddt, J=17.1, J=10.3, J=6.7, 1H); 5.52 (1H, bs); 5.05 (dq, J=17.1, J=1.6, 1H); 4.96 (dq, J=17.1, J=1.9, 1H); 3.72-3.65 (m, 1H); 2.31-1.52 (m, 14H).

$^{13}$C NMR: 138.6 (d); 134.7 (s); 125.0 (d); 114.6 (t); 68.0 (d); 46.5, 36.2, 30.12, 28.4, 25.3, 22.9, 22.4 (t).

Preparation of 1-(1-cyclohex-1-enyl)-5-hexen-2-one

Jones reagent (2.5 M, 1.7 ml, 4.3 mmol, 1.1 eq) was added slowly drop wise to a stirred solution of the alcohol (0.705 g, 3.92 mmol) in acetone (15 ml), after 5 minutes a further portion of the same Jones reagent (0.3 ml) was added and the suspension stirred for a further 15 minutes then poured into saturated sodium bicarbonate, extracted twice with pentane, washed with brine, then dried over anhydrous sodium sulfate, filtered and the solvents removed in vacuo. Further purification by bulb to bulb distillation (100° at 0.35 mbar) gave the desired ketone (73% yield).

$^1$H NMR: 5.81 (ddt, J=17.1, J=10.3, J=6.6, 1H); 5.55 (bs, 1H); 5.02 (dq, J=17.1, J=1.9, 1H); 4.97 (dq, J=10.3, J=1.5, 1H); 3.00 (s, 2H); 2.53 (t, J=7.3, 2H); 2.34-2.27 (m, 2H), 2.04 (bs, 2H); 1.91 (bs, 2H), 1.68-1.51 (m, 4H).

$^{13}$C NMR: 208 (s); 137.2 (d); 131.7 (s); 126.3 (d); 115.1 (t); 52.6, 40.7, 28.7, 27.8, 25.4, 22.8, 22.0 (t).

c) 1-Cyclopentyl-5-hexen-2-one

In a first 100 ml three necked round bottom flask 170 mg (3.9 mmol) lithium chloride and 310 mg (2.5 mmol) $MnCl_2$ were dissolved in 10 g THF and stirred for 2 hours at room temperature. After cooling to −5° C. 9.6 g (80 mmol) of pentenoyl chloride were added over the course of 30 minutes.

In a second 50 ml three necked round bottom flask 1.05 g (80 mmol) magnesium were suspended in 3 g THF. After heating to 60° C. 10 g (80 mmol) chloromethyl-cyclopentane dissolved in 7 g of THF were added. After stirring for further 30 minutes, this solution was pumped over the course of 1 hour onto the pentenoyl chloride solution at −5° C.

Stirring was continued for 1 hour and then the reaction mixture was slowly added to 35 g water. The organic phase was separated and the aqueous phase extracted with ether. The combined organic phases were washed with a saturated solution of sodium bicarbonate and then with water. After concentration the crude product was purified by distillation to give 1-cyclopentyl-5-hexen-2-one (yield=55%).

$^1$H-NMR: 5.80 (ddt, 1H), 5.02 (brd, 1H), 4.97 (brd, 1H), 2.50 (t, 2H), 2.43 (d, 2H), 2.32 (mc, 2H), 2.23 (mc, 1H), 1.81 (mc, 2H), 1.57 (mc, 4H), 1.08 (mc, 2H)

$^{13}$C-NMR: 210.2 (s), 137.2 (d), 115.1 (t), 49.2 (t), 42.0 (t), 35.6 (d), 32.6 (t), 27.8 (t), 25.0 (t)

d) 1-cyclohexyl-5-methyl-5-hexen-2-one

Preparation methyl 4-cyclohexyl-3-oxobutanoate

A 500 ml flask was charged with 120 g xylene, 33.8 g of solid potassium methylate (3.2 molar equivalent) and 34.0 g of dimethylcarbonate (2.5 molar equivalent). The slurry was heated to 50° C. and over the course of 4 hours 24.2 g of 1-cyclohexylpropan-2-one (87% GC, 1 molar equivalent) was added. Stirring was continued for 2 hours and then the reaction mixture was cooled to 25° C. 95 g of an acetic acid/water mixture (1:2) was then added carefully. After decantation the aqueous phase was drained and the organic phase concentrated. The crude product was distilled leading to 24.9 g of methyl 4-cyclohexyl-3-oxobutanoate (81% GC, 68% yield).

Preparation of 1-cyclohexyl-5-methylhex-5-en-2-one

A 250 ml flask was charged with 15.0 g of methyl 4-cyclohexyl-3-oxobutanoate (96% GC, 1 molar equivalent) and 9.8 g of methallyl chloride (1.5 molar equivalent). The mixture was heated to 70° C. and over the course of 90 minutes 13 g of a 30% solution of sodium methylate in methanol (1 molar equivalent) was added. Stirring was continued for 30 minutes and then 50 g of toluene was added. Within 1 hour 19.3 g of a 30% aqueous sodium hydroxide solution was added and stirring continued for 1 hour. After cooling to 25° C., 28.4 g of a 50% aqueous sulfuric acid solution was added over the course of 1 hour. To the slurry 70 g toluene and 40 g water were added and after decantation, the aqueous phase was drained. After concentration the crude product was fractionated leading to 8.9 g of 1-cyclohexyl-5-methylhex-5-en-2-one (95% GC, 60% yield).

$^{13}$C-NMR: 22.7 (q), 26.1 (t), 26.2 (t), 31.4 (t), 33.3 (t), 33.9 (d), 41.6 (t), 50.6 (t), 110.1 (t), 144.6 (s), 210.3 (s);

$^1$H-NMR: 4.72 (s, 1H), 4.65 (s, 1H), 2.53 (t, 2H), 2.29 (t, 2H), 2.27 (t, 2H), 1.84 (m, 1H), 1.73 (s, 3H), 1.71-1.61 (m, 5H), 1.28 (m, 2H), 1.13 (m, 1H), 0.92 (m, 2H)

Example 2

Preparation of a Perfuming Composition

An "eau de toilette" for man was prepared by admixing the following ingredients:

| Ingredient | Parts by weight |
|---|---|
| Geranyl acetate | 10 |
| Linalyl acetate | 420 |
| 10%* Anis aldehyde | 40 |
| 10%* C10 aldehyde | 10 |
| 10%* Ambrettolide | 20 |
| Butyl hydroxytoluene | 10 |
| 10%* Cardamom essential oil | 20 |
| Cetalox ®[1] Laevo | 120 |
| Citron Sfuma | 600 |
| Coumarine | 70 |
| 10%* Damascone Alpha[2] | 20 |
| (1'R,E)-2-ethyl-4-(2',2',3'-trimethyl-3'-cyclopenten-1'-yl)-2-buten-1-ol[3] | 70 |
| Dihydromyrcenol | 1650 |
| 10%* 2-Methyl-4-(2,2,3-trimethyl-3-cyclopenten-1-yl)-4-penten-1-ol[3] | 130 |
| Floralozone ®[4] | 20 |
| 10%* Galbanum Essential oil | 20 |
| Geraniol | 10 |
| Geranium China | 50 |
| Hedione ®[5] | 450 |
| 10%* 1,3-Benzodioxole-5-carbaldehyde | 10 |
| Lavandin Grosso | 130 |
| Linalool | 220 |
| Lyral ®[6] | 140 |
| 1-Methyl-4-(4-methyl-3-pentenyl)-3-cyclohexene-1-carbaldehyde | 20 |
| 10%* Terpineol Alpha | 40 |
| | 4300 |

*in dipropyleneglycol
[1])(-)-8,12-epoxy-13,14,15,16-tetranorlabdane; origin: Firmenich SA, Geneva, Switzerland
[2])(E)-1-(2,6,6-trimethyl-2-cyclohexen-1-yl)-2-buten-1-one; origin: Firmenich SA, Geneva, Switzerland
[3])origin: Firmenich SA, Geneva, Switzerland
[4])3-(4/2-ethylphenyl)-2,2-dimethylpropanal; origin: IFF, USA
[5])methyl dihydrojasmonate; origin: Firmenich SA, Geneva, Switzerland
[6])4/3-(4-hydroxy-4-methylpentyl)-3-cyclohexene-1-carbaldehyde; origin: IFF, USA The addition of 100 parts by weight of 1-cyclohexyl-5-hexen-2-one to the above-described eau de toilette conferred a touch particularly fruity, sweet pineapple leave, very balanced (especially on the sweet aspect).

Such balanced note was not obtained when other known perfuming ingredients were used instead of the invention's compound. Indeed, when to the above-described eau de toilette was added an allylic compound (e.g. allyl caproate, allyl cyclohexylpropionate or allyl heptenoate), it was obtained a note which was too sweet/sugar like.

When, it was added a glycolate derivative (e.g. allyl amyl glycolate), the note obtained was much greener, metallic earthy and honey like, lacking the equilibrium obtained using the invention's compound.

When, it was added 2-cyclohexyl-1,6-heptadien-3-one (see U.S. Pat. No. 6,184,419), the note obtained was much greener, galbanum (bitter, aromatic), almost pyrazinic and absolutely not fruity-pineapple, in other words the note final odor was totally different from the one obtained using the invention's compound.

Example 3

Preparation of a Perfuming Composition

A perfuming composition for a powder detergent was prepared by admixing the following ingredients:

| Ingredient | Parts by weight |
|---|---|
| Verdyl acetate | 150 |
| Anis aldehyde | 30 |
| Aspic essential oil | 30 |
| Benzophenone | 50 |
| Cetalox ®[1] | 20 |
| 4-Cyclohexyl-2-methyl-2-butanol | 240 |
| Damascone Alpha[2] | 20 |
| (1'R,E)-2-ethyl-4-(2',2',3'-trimethyl-3'-cyclopenten-1'-yl)-2-buten-1-ol[3] | 200 |
| Dihydromyrcenol | 1000 |
| Habanolide ®[4] | 400 |
| 1,3-Benzodioxole-5-carbaldehyde | 70 |
| 10%* 1-Phenylvinyl acetate[3] | 10 |
| Alpha Ionone | 200 |
| Iso E Super ®[5] | 500 |
| Methyl-iso-eugenol | 50 |
| Methylparacresol | 20 |
| Nirvanol ®[6] | 40 |
| Rose oxide | 10 |
| Phenethylol | 400 |
| Phenylhexanol | 250 |
| 9-Decen-1-ol | 40 |
| Sclareolate ®[7] | 600 |
| Terpineol | 250 |
| 4-Methyl-3-decen-5-ol | 30 |
| Verdox ®[8] | 100 |
| (2,2-Dimethoxyethyl)benzene | 20 |
| 10%** Violettyne[9] | 40 |
| 2,4-Dimethyl-3-cyclohexene-1-carbaldehyde | 30 |
| | 4800 |

*in dipropyleneglycol
**in isopropyl tetradecanoate
[1])8,12-epoxy-13,14,15,16-tetranorlabdane; origin: Firmenich SA, Geneva, Switzerland
[2])(E)-1-(2,6,6-trimethyl-2-cyclohexen-1-yl)-2-buten-1-one; origin: Firmenich SA, Geneva, Switzerland
[3])origin: Firmenich SA, Geneva, Switzerland
[4])pentadecenolide; origin: Firmenich SA, Geneva, Switzerland
[5])1-(octahydro-2,3,8,8-tetramethyl-2-naphthalenyl)-1-ethanone; origin: IFF, USA
[6])3,3-dimethyl-5-(2,2,3-trimethyl-3-cyclopenten-1-yl)-4-penten-2-ol; origin: Firmenich SA, Geneva, Switzerland
[7])propyl (S)-2-(1,1-dimethylpropoxy)propanoate; origin: Firmenich SA, Geneva, Switzerland
[8])2-tert-butyl-1-cyclohexyl acetate; origin: IFF, USA
[9])1,3-undecadien-5-yne; origin: Firmenich SA, Geneva, Switzerland The addition of 20 parts by weight of 1-cyclohexyl-5-hexen-2-one to the above-described perfuming composition conferred to the latter a fresh sweet, fruity-pineapple top note which is also persistent on a dry linen washed with a detergent comprising the perfuming composition.

What is claimed is:

1. A method to confer, enhance, improve or modify the odor properties of a perfuming composition or of a perfumed article, which method comprises adding to the composition or article an effective amount of at least one compound of formula I:

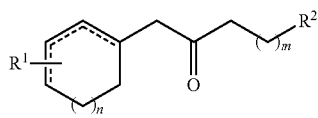

wherein n represents 0, 1 or 2;
m represents 0, 1 or 2;
the dotted lines represent only single bonds or one double bond and two single bonds;
$R^1$ represents a hydrogen atom or a methyl or ethyl group, said $R^1$ group being located at any of the position of the cyclic moiety;
$R^2$ represents a
$OR^3$ group, $R^3$ representing a $C_1$-$C_3$ alkyl or alkenyl group;
a group of formula $CR^4$=$C(R^4)_2$, $R^4$ representing, simultaneously or independently from each other, a hydrogen atom or a methyl or ethyl group; or
a group of formula

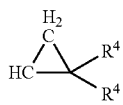

$R^4$ having the same meaning as above;
wherein the compound provides a fruity-pineapple note while being devoid of or not evoking galbanum notes.

2. The method according to claim 1, wherein the compound is of formula III:

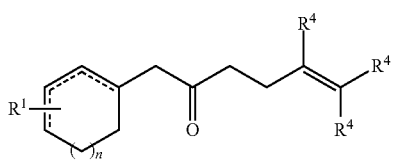

wherein n represents 0 or 1;
one dotted line represents a single or double carbon-carbon bond and the two other dotted lines represent a single carbon-carbon bond;
$R^1$ represents a hydrogen atom or a methyl group, said $R^1$ group being located at any of the position of the cyclic moiety;
$R^4$ representing, simultaneously or independently from each other, a hydrogen atom or a methyl group.

3. The method according to claim 1, wherein at least one $R^4$ is a hydrogen atom and $R^1$ represents a hydrogen atom.

4. The method according to claim 1, wherein the compound is of formula IV:

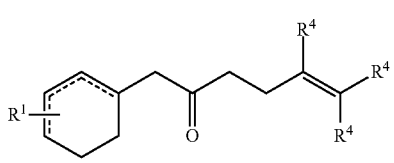

wherein one dotted line represents a single or double carbon-carbon bond and the two other dotted lines represent a single carbon-carbon bond;
$R^1$ represents a hydrogen atom or a methyl group, the $R^1$ group being located at any of the position of the cyclic moiety;
$R^4$ representing, simultaneously or independently from each other, a hydrogen atom or a methyl group.

5. The method according to claim 1, wherein the compound is 1-cyclohexyl-5-hexen-2-one or 1-(1-cyclohex-1-enyl)-5-hexen-2-one.

6. The method of claim 4, wherein in the compound $R^1$ is hydrogen.

7. The compound of claim 4, wherein in the compound each $R^4$ is hydrogen.

8. The method according to claim 1, wherein the odor properties of the perfuming composition or perfumed article are modified by providing a perfuming composition comprising:
i) at least one compound of formula (I);
ii) at least one ingredient selected from the group consisting of a perfumery carrier and a perfumery base; and
iii) optionally at least one perfumery adjuvant.

9. The method according to claim 1, wherein the odor properties of the perfuming composition or perfumed article are modified by providing a perfumed article comprising:
i) at least one compound of formula (I); and
ii) a consumer product base.

10. The method according to claim 9, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

11. A method to confer, enhance, improve or modify the odor properties of a perfuming composition or of a perfumed article, which method comprises adding to the composition or article an effective amount of 1-cyclohexyl-5-hexen-2-one or 1-(1-cyclohex-1-enyl)-5-hexen-2-one in order to provide a fruity-pineapple note while not imparting or providing galbanum notes.

12. The method according to claim 11, wherein the odor properties of the perfuming composition or perfumed article are modified by providing a perfuming composition comprising:
i) 1-cyclohexyl-5-hexen-2-one or 1-(1-cyclohex-1-enyl)-5-hexen-2-one;
ii) at least one ingredient selected from the group consisting of a perfumery carrier and a perfumery base; and
iii) optionally at least one perfumery adjuvant.

13. The method according to claim 12, wherein the odor properties of the perfuming composition or perfumed article are modified by providing a perfumed article comprising:

iii) 1-cyclohexyl-5-hexen-2-one or 1-(1-cyclohex-1-enyl)-5-hexen-2-one; and
iv) a consumer product base.

14. The method according to claim 11, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *